United States Patent
Chassot et al.

(10) Patent No.: US 6,461,388 B1
(45) Date of Patent: *Oct. 8, 2002

(54) DIAMINOBENZENE DERIVATIVE COMPOUNDS AND DYE COMPOSITIONS CONTAINING SAME

(75) Inventors: Laurent Chassot, Praroman; Laurence Descloux, Lovens, both of (CH)

(73) Assignee: Wella Aktiengesellschaft, Darmstadt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/541,937

(22) Filed: Apr. 3, 2000

(30) Foreign Application Priority Data

May 14, 1999 (DE) .......................... 199 22 392

(51) Int. Cl.⁷ ................................. A61K 7/13
(52) U.S. Cl. .................. 8/405; 8/405; 8/407; 8/408; 8/409; 544/180; 544/182; 544/242; 544/336; 546/329
(58) Field of Search ................. 544/180, 182, 544/242, 336; 546/329; 8/409, 408, 405, 407

(56) References Cited

U.S. PATENT DOCUMENTS

| | | | |
|---|---|---|---|
| 3,647,351 A | | 3/1972 | Lange |
| 4,994,087 A | * | 2/1991 | Konrad et al. .................. 8/409 |
| 6,132,475 A | * | 10/2000 | Chassot et al. .................. 8/409 |

FOREIGN PATENT DOCUMENTS

| | | |
|---|---|---|
| DE | 25 18 393 | 4/1976 |
| DE | 42 34 886 A1 | 4/1994 |
| DE | 198 22 041 A1 | 12/1999 |
| EP | 0 740 931 A1 | 11/1996 |
| EP | 0 943 614 A2 | 9/1999 |
| EP | 0 963 982 A2 | 12/1999 |

OTHER PUBLICATIONS

Protection for the amino group—"Protective Group"–Organic Synthesis Chapter 7,. Wiley Interscience.–1991.
J.J.S. Lamba and J.M. Tour: "Imine–Bridged Planar Poly (P–Phenylene) Derivatives for Maximization . . . ", in American Chamical Society 1994, 116 pp. 11723–11736.

* cited by examiner

Primary Examiner—Yogendra N. Gupta
Assistant Examiner—Eisa Elhilo
(74) Attorney, Agent, or Firm—Michael J. Striker

(57) ABSTRACT

New p-diaminobenzene derivative compounds of formula (I), or their physiologically compatible salts, are disclosed:

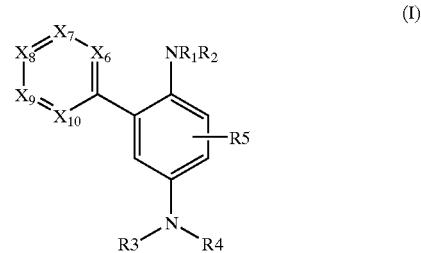

Compositions for oxidatively dyeing keratin fibers, especially human hair, that contain the p-diaminobenzene derivative compounds of formula (I), as well as a suitable coupler substance, are also disclosed.

14 Claims, No Drawings

DIAMINOBENZENE DERIVATIVE COMPOUNDS AND DYE COMPOSITIONS CONTAINING SAME

BACKGROUND OF THE INVENTION

1. Field of the Invention

The present invention relates to new p-diaminobenzene derivative compounds and compositions for dyeing keratin fibers containing these new compounds.

2. Prior Art

Oxidation dye compounds have long attained substantial importance in the art of dyeing keratin fibers, especially hair dyeing. The dyeing caused by those compounds occurs by reaction of certain developer substances with certain coupler substances in the presence of a suitable oxidizing agent. For example, 2,5-diaminotoluene, 2,5-diaminophenylethyl alcohol, p-aminophenol and 1,4-diaminobenzene can be used as developer substances, while resorcinol, 4-chlororesorcinol, 1-naphthol, 3-aminophenol and derivatives of m-phenylendiamine can be mentioned as coupler substances.

There are numerous additional requirements for oxidation dye compounds that are used to dye human hair besides color in the desired intensity. Thus the dye compounds must be unobjectionable in regard to toxicological and dermatological properties and must provide the desired hair color with a good light fastness, fastness to a permanent wave treatment, acid fastness and fastness to rubbing. The color of the hair dyed with the dye compounds in each case must be stable for at least 4 to 6 weeks to light, rubbing and chemical agents. Furthermore an additional requirement is the production of a broad palette of different color shades using different developer and coupler substances.

It is not possible to fulfill all the above-mentioned requirements with the currently known dye compounds.

SUMMARY OF THE INVENTION

It is an object of the present invention to provide improved developer compounds that fulfill the above-described requirements in a special manner.

It has now been surprisingly found that the new p-diaminobenzene derivative compounds according to formula (I) fulfill the many requirements for developer compounds to an especially great extent. Particularly bright or intense color shades are produced using these developer substances with predominantly known coupler substances, which are however extraordinarily light fast and fast to washing.

The subject matter of the present invention is thus p-diaminobenzene derivative compounds of the following formula (I), or their physiologically compatible water-soluble salts:

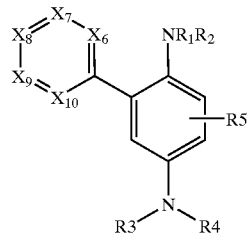
(I)

wherein $X_6$, $X_7$, $X_8$, $X_9$, $X_{10}$, each, independently of each other, represents nitrogen or C—R6, C—R7, C—R8, C—R9, C—R10, with the proviso that at least one and at most three of the groups, $X_6$, $X_7$, $X_8$, $X_9$, $X_{10}$, represent nitrogen and R6, R7, R8, R9, R10 each, independently of each other, represents hydrogen, a halogen atom, a cyano group, a hydroxy group, a $C_1$- to $C_4$-alkoxy group, a $C_1$- to $C_6$-alkyl group, a $C_1$- to $C_4$-alkylthioether group, a mercapto group, a nitro group, an amino group, a $C_1$- to $C_4$-alkylamino group, a di($C_1$- to $C_4$-)alkylamino group, a trifluoromethane group, a —C(O)H group, a —C(O)CH$_3$ group, a —C(O)CF$_3$ group, a —Si(CH$_3$)$_3$ group, a —C(O)NH$_2$ group, a $C_1$- to $C_4$-hydroxyalkyl group, a $C_3$- to $C_4$-dihydroxyalkyl group, a —CH═CHR11 group, a —(CH$_2$)$_p$—CO$_2$R12 group or a —(CH$_2$)$_p$R13 group with p=1, 2, 3 or 4, a —C(R14)═NR15 group or a —C(R17)H—NR18R19 group;

R1, R2, R3 and R4 each, independently of each other, represents hydrogen, a $C_1$- to $C_6$-alkyl group, a $C_1$- to $C_4$-hydroxyalkyl group, a $C_2$- to $C_4$-dihydroxyalkyl group or a $C_1$- to $C_4$-alkoxy-($C_1$- to $C_4$)-alkyl group or R1 and R2 or R3 and R4 represent a four-membered to eight-membered aliphatic ring, with the proviso that at least two of the R1 to R4 groups represent hydrogen;

R5 represents hydrogen, a hydroxy group, a halogen atom, a $C_1$- to $C_4$-alkyl group, a $C_1$- to $C_4$-hydroxyalkyl group or a $C_1$- to $C_4$-alkoxy group;

R11 represents hydrogen, a hydroxy group, an amino group, a —CO$_2$R12 or a —C(O)CH$_3$ group;

R12, R14 and R17 each, independently of each other, represents hydrogen or a $C_1$- to $C_4$-alkyl group;

R13 represents an amino group or a nitrile group;

R15, R18 and R19 each, independently of each other, represents hydrogen, a hydroxy group, a $C_1$- to $C_4$-alkyl group, a $C_1$- to $C_4$-hydroxyalkyl group, a $C_3$- to $C_4$-dihydroxyalkyl group or a group of the formula:

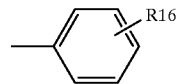

and

R16 represents hydrogen, an amino group or a hydroxy group.

Examples of the compounds of formula I are: 2,5-diamino-1-(2-pyridyl)benzene; 2,5-diamino-1-(3-pyridyl)benzene; 2,5-diamino-1-(4-pyridyl)benzene; 2,5-diamino-4-methoxy-1-(2-pyridyl)benzene; 2,5-diamino-4-methoxy-1-(3-pyridyl)benzene; 2,5-diamino-4-methoxy-1-(4-pyridyl)benzene; 2,5-diamino-4-methyl-1-(2-pyridyl)benzene; 2,5-diamino-4-methyl-1-(3-pyridyl)benzene; 2,5-diamino-4-methyl-1-(4-pyridyl)benzene; 2,5-diamino-1-(3-amino-2-pyridyl)benzene; 2,5-diamino-1-(3-chloro-2-pyridyl)benzene; 2,5-diamino-1-(3-fluoro-2-pyridyl)benzene; 2,5-diamino-1-(3-hydroxy-2-pyridyl)benzene; 2,5-diamino-1-(3-methyl-2-pyridyl)benzene; 2,5-diamino-1-(3-trifluoromethyl-2-pyridyl)benzene; 2,5-diamino-1-(4-amino-2-pyridyl)benzene; 2,5-diamino-1-(4-chloro-2-pyridyl)benzene; 2,5-diamino-1-(4-fluoro-2-pyridyl)benzene; 2,5-diamino-1-(4-hydroxy-2-pyridyl)benzene; 2,5-diamino-1-(4-methyl-2-pyridyl)benzene; 2,5-diamino-1-(4-trifluoromethyl-2-pyridyl)benzene; 2,5-diamino-1-(5-amino-2-pyridyl)benzene; 2,5-diamino-1-(5-chloro-2-pyridyl)benzene; 2,5-diamino-1-(5-fluoro-2-pyridyl)benzene; 2,5-diamino-1-(5-hydroxy-2-pyridyl)benzene; 2,5-diamino-1-(5-methyl-2-pyridyl)benzene; 2,5-diamino-1-(5- trifluoromethyl-2-pyridyl)benzene; 2,5-diamino-1-(6-amino-2-pyridyl)benzene; 2,5-diamino-1-(6-chloro-2-pyridyl)benzene; 2,5-diamino-1-(6-fluoro-2-pyridyl)benzene; 2,5-diamino-1-(6-hydroxy-2-pyridyl)benzene; 2,5-diamino-1-(6-methyl-2-pyridyl)benzene; 2,5-diamino-1-(6-trifluoromethyl-2-pyridyl)benzene; 2,5-diamino-1-(2-amino-3-pyridyl)benzene; 2,5-diamino-1-(2-chloro-3-pyridyl)benzene; 2,5-diamino-1-(2-fluoro-3-pyridyl)benzene; 2,5-diamino-1-(2-hydroxy-3-pyridyl)benzene; 2,5-diamino-1-(2-methyl-3-pyridyl)benzene; 2,5-diamino-1-(2-trifluoromethyl-3-pyridyl)benzene; 2,5-diamino-1-(4-amino-3-pyridyl)benzene; 2,5-diamino-1-(4-chloro-3-pyridyl)benzene; 2,5-diamino-1-(4-fluoro-3-pyridyl)benzene; 2,5-diamino-1-(4-hydroxy-3-pyridyl)benzene; 2,5-diamino-1-(4-methyl-3-pyridyl)benzene; 2,5-diamino-1-(4-trifluoromethyl-3-pyridyl)benzene; 2,5-diamino-1-(5-amino-3-pyridyl)benzene; 2,5-diamino-1-(5-chloro-3-pyridyl)benzene; 2,5-diamino-1-(5-fluoro-3-pyridyl)benzene; 2,5-diamino-1-(5-hydroxy-3-pyridyl)benzene; 2,5-diamino-1-(5-methyl-3-pyridyl)benzene; 2,5-diamino-1-(5-trifluoromethyl-3-pyridyl)benzene; 2,5-diamino-1-(6-amino-3-pyridyl)benzene; 2,5-diamino-1-(6-chloro-3-pyridyl)benzene; 2,5-diamino-1-(6-fluoro-3-pyridyl)benzene; 2,5-diamino-1-(6-hydroxy-3-pyridyl)benzene; 2,5-diamino-1-(6-methyl-3-pyridyl)benzene; 2,5-diamino-1-(6-trifluoromethyl-3-pyridyl)benzene; 2,5-diamino-1-(2-amino-4-pyridyl)benzene; 2,5-diamino-1-(2-chloro-4-pyridyl)benzene; 2,5-diamino-1-(2-fluoro-4-pyridyl)benzene; 2,5-diamino-1-(2-hydroxy-4-pyridyl)benzene; 2,5-diamino-1-(2-methyl-4-pyridyl)benzene; 2,5-diamino-1-(2-trifluoromethyl-4-pyridyl)benzene; 2,5-diamino-1-(3-amino-4-pyridyl)benzene; 2,5-diamino-1-(3-chloro-4-pyridyl)benzene; 2,5-diamino-1-(3-fluoro-4-pyridyl)benzene; 2,5-diamino-1-(3-hydroxy4-pyridyl)benzene; 2,5-diamino-1-(3-methyl-4-pyridyl)benzene; 2,5-diamino-1-(3-trifluoromethyl-4-pyridyl)benzene; 2,5-diamino-1-(5-amino-4-pyridyl)benzene; 2,5-diamino-1-(5-chloro-4-pyridyl)benzene; 2,5-diamino-1-(5-fluoro-4-pyridyl)benzene; 2,5-diamino-1-(5-hydroxy-4-pyridyl)benzene; 2,5-diamino-1-(5-methyl-4-pyridyl)benzene; 2,5-diamino-1-(5-trifluoromethyl4-pyridyl)benzene; 2,5-diamino-1-(6-amino-4-pyridyl)benzene; 2,5-diamino-1-(6-chloro-4-pyridyl)benzene; 2,5-diamino-1-(6-fluoro-4-pyridyl)benzene; 2,5-diamino-1-(6-hydroxy-4-pyridyl)benzene; 2,5-diamino-1-(6-methyl-4-pyridyl)benzene; 2,5-diamino-1-(6-trifluoromethyl-4-pyridyl)benzene; 2,5-diamino-1-(2-pyrimidyl)benzene; 2,5-diamino-1-(4-pyrimidyl)benzene; 2,5-diamino-1-(5-pyrimidyl)benzene; 2,5-diamino-1-(6-pyrimidyl)benzene; 2-hydroxyethylamino-5-amino-1-(2-pyridyl)benzene; 2-hydroxyethylamino-5-amino-1-(2-pyridyl)benzene; 2-hydroxyethylamino-5-amino-1-(3-pyridyl)benzene; 2-hydroxyethylamino-5-amino-1-(4-pyridyl)benzene; 2-bis-(hydroxyethyl)amino-5-amino-1-(2-pyridyl)benzene; 2-bis-(hydroxyethyl)amino-5-amino-1-(3-pyridyl)benzene; 2-bis-(hydroxyethyl)amino-5-amino-1-(4-pyridyl)benzene; 2,5-diamino-1-(3-cyano-2-pyridyl)benzene; 2,5-diamino-1-(3-nitro-2-pyridyl)benzene; 2,5-diamino-1-(4-cyano-2-pyridyl)benzene; 2,5-diamino-1-(4-nitro-2-pyridyl)benzene; 2,5-diamino-1-(5-cyano-2-pyridyl)benzene; 2,5-diamino-1-(5-nitro-2-pyridyl)benzene; 2,5-diamino-1-(6-cyano-2-pyridyl)benzene; 2,5-diamino-1-(6-nitro-2-pyridyl)benzene; 2,5-diamino-1-(2-cyano-4-pyridyl)benzene; 2,5-diamino-1-(2-nitro-4-pyridyl)benzene; 2,5-diamino-1-(3-cyano-4-pyridyl)benzene; 2,5-diamino-1-(3-nitro-4-pyridyl)benzene; 2,5-diamino-1-(5-cyano-4-pyridyl)benzene; 2,5-diamino-1-(5-nitro-4-pyridyl)benzene; 2,5-diamino-1-(6-cyano-4-pyridyl)benzene; 2,5-diamino-1-(6-nitro-4-pyridyl)benzene; 2,5-diamino-1-(2-cyano-3-pyridyl)benzene; 2,5-diamino-1-(2-nitro-3-pyridyl)benzene; 2,5-diamino-1-(4-cyano-3-pyridyl)benzene; 2,5-diamino-1-(4-nitro-3-pyridyl)benzene; 2,5-diamino-1-(5-cyano-3-pyridyl)benzene; 2,5-diamino-1-(5-nitro-3-pyridyl)benzene; 2,5-diamino-1-(6-cyano-3-pyridyl)benzene and 2,5-diamino-1-(6-nitro-3-pyridyl)benzene or their physiologically compatible salts.

Preferred compounds of formula (I) are those in which (i) R1 and R2 or R3 and R4 or all the group R1 to R4 represent hydrogen; and/or (ii) 1 or 2 of the groups $X_6$ to $X_{10}$ are nitrogen and the remaining groups $X_6$ to $X_{10}$ are C—R, wherein in one of these C—R groups R represents hydrogen, halogen, a $C_1$–$C_4$ alkyl group or a $C_1$–$C_4$ hydroxyalkyl group, while in the other C—R groups R represents hydrogen; and/or (iii) R5 reprsents hydrogen.

Especially preferred p-diaminobenzene derivative compounds of formula (I) include: 2,5-diamino-1-(2-pyridyl)benzene; 2,5-diamino-1-(3-pyridyl)benzene; 2,5-diamino-1-(4-pyridyl)benzene; 2,5-diamino-1-(2-pyrimidyl)benzene; 2,5-diamino-1-(6-methyl-2-pyridyl)benzene; 2,5-diamino-1-(4-methyl-2-pyridyl)benzene; 2,5-diamino-1-(5-methyl-2-pyridyl)benzene and 2,5-diamino-1-(3-methyl-2-pyridyl)benzene or their physiologically compatible salts.

The compound of formula (I) can be used as free bases and also in the form of their physiologically compatible salts with inorganic or organic acids, such as hydrochloric acid, sulfuric acid, phosphoric acid, acetic acid, propionic acid, lactic acid or citric acid.

The diaminobenzene derivative compounds of formula (I) can be prepared using the following known synthesis scheme:

The synthesis of the compounds according to the invention can for example be performed:

Either (a) by a tetrakis(triphenylphosphine)palladium catalyzed coupling of a substituted benzene of the formula (II):

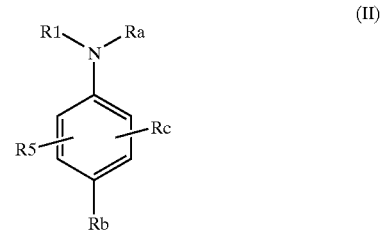

with the heterocyclic compound of formula (III):

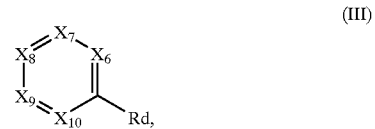

and subsequently splitting off the protective group or splitting off the protective group and reduction of the nitro group; or (b) by a tetrakis(triphenylphosphine)palladium coupling of a substituted benzene of formula (IV):

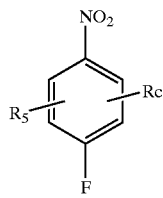

(IV)

with a heteroaryl compound of the formula (III)

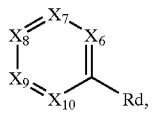

(III)

and subsequent substitution of the obtained substituted benzene compound of the formula (V):

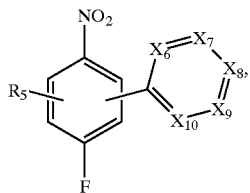

(V)

with an amine group of the formula HNR1R2 and subsequent reduction of the nitro group.

The remaining groups used in formulae (II) to (V) have the following significance:

Ra represents a protective group, as described, for example, in the chapter, "Protective Groups", in Organic Synthesis, Chapter 7, Wiley Interscience, 1991.

Rb represents NR1Ra or $NO_2$;

Rc represents halogen and Rd represents $B(OH)_2$ or

Rc represents $B(OH)_2$ and Rd represents halogen; and

R1, R2, R5, $X_6$, $X_7$, $X_8$, $X_9$ and $X_{10}$ have the same significance as in formula (I).

The diaminobenzene derivative compounds of formula (I) are water-soluble and permit dyeing with great color intensity and outstanding fastness, especially light-fastness, wash-fastness and fastness to rubbing. The compounds of formula (I) have outstanding storage stability, especially as ingredients of the dye compositions described in the following disclosure.

The subject matter of the invention also includes compositions for oxidative dyeing of keratin fibers, for example hair, fur, feathers or wool, especially human hair, based on a developer-coupler combination which includes at least one diaminobenzene derivative compound of the above formula (I) as developer substance.

The diaminobenzene derivative compound of formula (I) is contained in the dye composition according to the invention in an amount of from about 0.005 to 20 percent by weight, preferably however from about 0.01 to 5.0 percent by weight, and especially preferably from 0.1 to 2.5 percent by weight.

The coupler substance preferably can be 2,6-diaminopyridine, 2-amino-4-[(2-hydroxyethyl)amino] anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino) pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di(2-hydroxyethoxy)-benzene, 1-(2-aminoethoxy)-2,4-diaminobenzene, 2-amino-1-(2-hydroxyethoxy)-4-methylaminobenzene, 2,4-diaminophenoxyacetic acid, 3-[(di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy) methane, 1,3-diamino-2,4-dimethoxybenzene, 2,6-bis-(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methyphenol, 5-amino-4-ethoxy-2-methylphenol, 3-amino-2,4-dicholorophenol, 5-amino-2,4-dichlorophenol, 3-amino-2-methylphenol, 3-amino-2-chloro-6-methylphenol, 3-aminophenol, 2-{(3-hydroxyphenyl)amino]acetamide, 5-[(2-hydroxyethyl) amino]-2-methylphenol, 3-[(2-hydroxyethyl)aminophenol, 3-[(2-methoxyethyl)amino]phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methy-phenol, 1-naphthol, 1,5-dihydroxynaphthalene, 1,7-dihydroxynaphthalene, 2,3-dihydoxynaphthalene, 2,7-dihydoxynaphthalene, 2-methyl-1-naphthaol acetate, 1,3-dihydoxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxy-phenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolindione.

Although the advantageous properties of the above-described diaminobenzene derivative compounds of formula (I) can obviously be obtained when the diaminobenzene derivative compounds of formula (I) are used alone, it is understandably also possible to use the diaminobenzene derivative compounds of formula (I) together with known developer substances, such as 1,4-diaminobenzene, 2,5-diaminotoluene, 2,5-diaminophenylethyl alcohol, 4-aminophenol and its derivatives, especially 4-amino-3-methylphenol, 4,5-diamino-1-(2-hydroxyethyl)pyrazole or tetraaminopyrimidines.

The coupler and developer substances can be contained in the dye compositions according to the invention individually, or in mixtures with each other. The total amount of coupler substances and developer substances in the dye composition according to the invention (relative to the total amount of the dye composition) is from about 0.005 to 20 percent by weight respectively, preferably from about 0.01 to 5.0 percent by weight and especially preferably from 0.1 to 2.5 percent by weight.

The total amount of the combination of developer and coupler substances in the dye composition described here is preferably from about 0.01 to 20 percent by weight, especially preferably from about 0.02 to 10 percent by weight, and most preferably from 0.2 to 6.0 percent by weight. The developer and coupler substances are used generally in equimolar amounts, however it is not disadvantageous when the developer substances are present in a certain excess or deficiency(for example in a coupler substance to developer substance ratio of 1:2 to 1:0.5).

The dye compositions according to the invention can also contain certain other dye ingredients, for example 6-amino-2-methylphenol and 2-amino-5-methylphenol, as well as conventional direct-dyeing dye compounds, such as triphenylmethane dye compounds, such as 4-[(4'-aminophenyl)-(4'-imino-2",5"-cyclohexadien-1"-yliden)-methyl]-2-methylaminobenzene monohydrochloride (C.I. 42 510) and 4-[(4'-amino-3'-methylphenyl)-(4"-imino-2",5"-cyclohexadien-1"-yliden)methyl]-2-methylaminobenzene mono-hydrochloride (C.I. 42 520); aromatic nitro dye compounds, such as 4-(2'-hydroxyethyl)aminonitrotoluene, 2-amino-4,6-dinitrophenol, 2-amino-5-(2'-hydroxyethyl) aminonitrobenzene, 2-chloro-6-(ethylamino)-4-nitrophenol, 4-chloro-N-(2-hydroxyethyl)-2-nitroaniline, 5-chloro-2-hydroxy-4-nitroaniline, 2-amino-4-chloro-6-nitro-phenol and 1-[(2'-ureidoethyl)amino-4-nitrobenzene; azo dye compounds, such as 6-[(4'-aminophenyl)azo]-5-hydroxynapththalen-1-sulfonic acid sodium salt (C.I. 14 805) and dispersion dye compounds, such as 1,4-diaminoanthraquinone and 1,4,5,8-tetraaminoanthraquinone. These dye compounds can be contained in the dye composition of the invention in an amount of from about 0.1 to 4.0 percent by weight.

Understandably the coupler substances and the developer substances as well as the other dye compounds, in so far as they are bases, can also be used in the form of their physiologically compatible salts with organic or inorganic acids, such as hydrochloric acid or sulfuric acid, or, in so far as they have aromatic OH groups, in the form of their salts with bases, such as alkali phenolates.

Moreover cosmetic additive ingredients, which are commonly used in compositions for dyeing hair, can be used in the dye compositions according to the invention, for example antioxidants, such as ascorbic acid, thioglycolic acid or sodium sulfite, and perfume oils, complex formers, wetting agents, emulsifiers, thickeners and care materials. The form of the dye compositions according to the invention can be, for example, a solution, especially an aqueous or aqueous-alcoholic solution. However the form that is particularly preferred is a cream, gel or an emulsion. Its composition is a mixture of the dye ingredients with the conventional cosmetic additive ingredients suitable for the particular preparation.

Conventional cosmetic additive ingredients in solutions, creams, emulsion or gels include, for example, solvents, such as water, lower aliphatic alcohols, such as ethanol, propanol or isopropanol, glycerol or glycols, such as 1,2-propylene glycol, wetting agents or emulsifiers from the classes of anionic, cationic, amphoteric or nonionic surfactant compounds, such as fatty alcohol sulfates, ethoxylated fatty alcohol sulfates, alkylsulfonates, alkylbenzenesulfonates, alkyltrimethylammonium salts, aklylbetaines, ethoxylated fatty alcohols, ethoxylated nonylphenols, fatty acid alkanol amides and ethoxylated fatty acid esters; thickeners, such as higher fatty alcohols, starches, cellulose derivatives, petrolatum, paraffin oil and fatty acids, as well as care materials, such as cationic resins, lanolin derivatives, cholesterol, pantothenic acid and betaine. The above-mentioned conventional cosmetic ingredients are used in amounts suitable for their purposes. For example, the wetting agents and emulsifiers are used in concentrations of from about 0.5 to 30 percent by weight, the thickeners are used in an amount of from about 0.1 to 25 percent by weight and the care materials are used in concentrations of from about 0.1 to 5.0 percent by weight.

The dye compositions according to the invention can be weakly acidic, neutral or alkaline according to their composition. The compositions preferably have a pH from 5 to 11.5, especially preferably from 6.8 to 10.5. Their pH can be adjusted in the basic range with ammonia. Also organic amines can be used for this purpose, including monoethanolamine and triethanolamine, or also inorganic bases, such as sodium hydroxide and potassium hydroxide. Inorganic or organic acids can be used for adjusting the pH in the acid range, for example phosphoric acid, acetic acid, citric acid or tartaric acid.

In order to use the oxidation hair dye composition for dyeing hair the above-described dye compositions according to the invention are mixed with an oxidizing agent immediately prior to use and an amount of the mixture sufficient to dye the hair is applied to the hair, according to the hair abundance, generally from about 60 to 200 grams.

Principally hydrogen peroxide, or its addition compounds with urea, melamine, sodium borate or sodium carbonate, can be used in the form of a 3 to 12 percent, preferably 6 percent, aqueous solution as the oxidizing agent for developing the hair dye. Air oxygen can also be used as the oxidizing agent. If a 6 percent hydrogen peroxide solution is used as oxidizing agent, the weight ratio of hair dye composition and oxidizing agent is 5:1 to 1:2, but preferably 1:1. Larger amounts of oxidizing agent are used above all with larger dye concentrations in the hair dye composition, or when at the same time a strong bleaching of the hair is desired. The mixture of the oxidizing agent and the dye composition of the invention is allowed to act on the hair for about 10 to 45 minutes, preferably 30 minutes, at 15 to 50 degrees Celsius. The hair is then rinsed with water and dried. If necessary it is washed with a shampoo and eventually after-rinsed with a weak organic acid, such as citric acid or tartaric acid. Subsequently the hair is dried.

The hair dye composition according to the invention with a content of diaminobenzene derivative compounds of formula (I) as developer substance permits hair dyeing with outstanding color fastness, especially light fastness, fastness to washing and fastness to rubbing. The dye composition according to the invention provides a broad palette of different color shades, which extend from blond to brown, purple, violet to blue and black shades, according to the type and composition of the dye compounds in it. Particularly the color shades produced have outstanding color intensity. The very good dyeing properties of the compositions according to the invention include the production of good color coverage and dyeing of gray, chemically not-previously damaged hair without problems.

The following examples should serve to illustrate the invention, but details present in these examples should not be considered as further limiting the following appended claims, unless they are explicitly included in the following appended claims.

EXAMPLES

I. Production Examples

Example 1: Synthesis of 2,5-diamino-1-pyridylbenzene Compounds of Formula (I)
(General Synthetic Recipe)

A. Synthesis of 2,5-tert-butyloxycarbonylaminobromobenzene 15.65 g (0.07 mol)bromo-p-phenylenediamine hydrochloride and 32.7 g (0.15 mol)di-tert.-butyl-dicarbonate are dissolved in a mixture of 250 ml 2N sodium hydroxide and 250 ml trifluorotoluene and heated at 45° C. This reaction mixture is stirred for 3 days. Then 30 g (0.14 mol) di-tert.butyl dicarbonate is added stepwise. Subsequently the organic layer is separated and the aqueous phase is extracted twice with 100 ml dichloromethane. The combined extracts are evaporated to dryness and the residue is taken up in 200 ml of hexane. The precipitate is filtered and washed with 50 ml hexane. 18.6 g (82% of theoretical) of 2,5-tert.-butyloxycarbonylamino-bromobenzene is obtained with a melting point of 130° C.

B. Synthesis of 2,5-diamino-1-pyridylbenzene Compounds of Formula (I)

3.3 g (0.01 mol) 2,5-tert.-butyloxycarbonylaminobromobenzene from step A and 0.013 mol of an appropriate boric acid are dissolved in 70 ml of 1,2-dimethoxyethane under argon. Subsequently 0.5 g tetrakis(triphenylphosphine)palladium (0.0005 mol) and 13 ml 2N potassium carbonate are added and the resulting reaction mixture is heated to 80° C. After termination of the reaction, the reaction mixture is poured into 100 ml acetic acid ethyl ester, the organic phase is extracted with dilute sodium hydroxide and then dried with magnesium sulfate. The solvent is distilled off in a rotary evaporator and the residue is purified on silica gel with petroleum ether/acetic acid ethyl ester (9:1). The product obtained in this way is heated to 50° C. in ethanol. Then 15 ml of a 2.9 molar ethanolic hydrochloric acid solution is added dropwise to make the hydrochloride salt. The precipitate is filtered, washed twice with 10 ml ethanol and then dried.

2.5-diamino-1-(3-pyridyl)benzene Trihydrochloride
  Boric acid used: 3-pyridyl-boric acid
  Yield: 1.3 g (45% of theoretical)
  Melting Point: 250° C. (decomposes) (colorless crystals)

| CHN Analysis: | | | |
|---|---|---|---|
| $C_{11}H_{14}N_3Cl_3$ | % C | % H | % N |
| Calculated | 44.85 | 4.79 | 14.26 |
| Found | 45.56 | 4.26 | 14.09 |

Example 2: Synthesis of 2,5-diamino-1-pyridylbenzene Compounds and 2,5-diamino-1-(2-pyrimidyl)benzene Compounds of Formula (I) (General Synthetic Recipe)

A. Synthesis of N,N-bis-(tert-butoxycarbonyl)-2,5-diamino-1-phenylboric Acid

The N,N-bis-(tert-butoxycarbonyl)-2,5-diamino-1-phenylboric acid is made by reaction of N,N-bis-(tert-butoxycarbonyl)-2,5-diamino-1-bromobenzene with tert-butyllithium and trimethylborate. The experimental recipe for the preparation is described by J. M. Tour and J. J. S. Lamba in J. Am. Chem. Soc. 1994, 116, p. 11723.

B. Synthesis of 2,5-diamino-1-pyridylbenzene Compounds and 2,5-diamino-1-(2-pyrimidyl)benzene Compounds of Formula (I)

0.035 g (0.0001 mol) of N,N-bis(tert-butoxycarbonyl)-2,5-diamino-1-phenylboric acid from step A and 0.00015 mol of the corresponding bromo-derivative compound are dissolved in 10 ml of 1,2-dimethoxyethane under argon. Subsequently 0.005 g tetrakis(triphenylphosphine)-palladium (0.000005 mol) and 0.13 ml 2N potassium carbonate are added and the resulting reaction mixture is heated to 80° C. After termination of the reaction, the reaction mixture is poured into 10 ml acetic acid ethyl ester, the organic phase is extracted with dilute sodium hydroxide and then dried with magnesium sulfate. The solvent is distilled off in a rotary evaporator and the residue is purified on silica gel with petroleum ether/acetic acid ethyl ester (9:1). The product obtained in this way is heated to 50° C. in 4 ml ethanol. Then 1.5 ml of a 2.9 molar ethanolic hydrochloric acid solution is added dropwise to make the hydrochloride salt. The precipitate is filtered, washed twice with 1 ml ethanol and then dried.

a. 2,5-diamino-1-(3-methyl-2-pyridyl)benzene Hydrochloride
  Bromo derivative used: 2-bromo-3-methylpyridine
  Yield: 0.025 g (81% theoretical)
  Mass spectra MH$^+$ 200(100)

b. 2,5-diamino-1-(5-carboamido-3-pyridyl)benzene Hydrochloride
  Bromo derivative used: 5-bromo-nicotinamide
  Yield: 0.025 g (74% theoretical)
  Mass spectra MH$^+$ 229(100)

c. 2,5-diamino-1-(6-methyl-2-pyridyl)benzene Hydrochloride
  Bromo derivative used: 2-bromo-6-methylpyridine
  Yield: 0.025 g (81% theoretical)
  Mass spectra MH$^+$ 200(100)

d. 2.5-diamino-1-(3-trifluoromethyl-2-pyridyl)benzene Hydrochloride
  Bromo derivative used: 2-bromo-3-trifluoromethylpyridine
  Yield: 0.025 g (69% theoretical)
  Mass spectra MH$^+$ 254(100)

e. 2,5-diamino-1-(2-pyridyl)benzene Hydrochloride
  Bromo derivative used: 2-bromopyridine
  Yield: 0.025 g (85% theoretical)
  Mass spectra MH$^+$ 186(100)

f. 2,5-diamino-1-(5-cyano-3-pyridyl)benzene Hydrochloride
  Bromo derivative used: 3-bromo-5-cyanopyridine
  Yield: 0.025 g (88% theoretical)
  Mass spectra MH$^+$ 238(100)

g. 2,5-diamino-1-(5-methyl-2-pyridyl)benzene Hydrochloride
  Bromo derivative used: 2-bromo-5-methylpyridine
  Yield: 0.025 g (81% theoretical)
  Mass spectra MH$^+$ 200(100)

h. 2,5-diamino-1-(4-methyl-2-pyridyl)benzene Hydrochloride
  Bromo derivative used: 2-bromo-4-methylpyridine
  Yield: 0.025 g (81% theoretical)
  Mass spectra MH$^+$ 200(100)

i. 2,5-diamino-1-(5-trifluoromethyl-2-pyridyl)benzene Hydrochloride
  Bromo derivative used: 2-bromo-5-trifluoromethylpyridine
  Yield: 0.025 g (69% theoretical)
  Mass spectra MH$^+$ 254(100)

j. 2,5-diamino-1-(5-nitro-2-pyridyl)benzene Hydrochloride
  Bromo derivative used: 2-bromo-5-nitropyridine
  Yield: 0.025 g (74% theoretical)
  Mass spectra MH$^+$ 231(100)

k. 2,5-diamino-1-(2-pyrimidyl)benzene Hydrochloride
  Bromo derivative used: 2-bromopyrimidine
  Yield: 0.025 g (74% theoretical)
  Mass spectra MH$^+$ 231(100)

II. Examples of Hair Dye Compositions

Examples 3 to 6: Hair Dye Compositions

Hair Dye Solutions were prepared having the following composition:

| | | |
|---|---|---|
| 0.00125 mol | developer substance according to Table I | |
| 0.00125 mol | coupler substance according to Table I | |
| 10.0 g | potassium oleate (8% aqueous solution) | |
| 10.0 g | ammonia (22 percent aqueous solution) | |
| 10.0 g | isopropanol | |
| 0.3 g | ascorbic acid | |
| to 100.0 g | water | |

30 g of the above-described dye solution were mixed immediately prior to use with 30 g of 6 percent hydrogen peroxide solution. Then the mixture was applied to bleached hair. After an acting time of 30 minutes at 40° C., the hair was rinsed with water, washed with a shampoo and dried. The resulting colors for the dyeing hair are summarized in the following Table I.

TABLE I

HAIR DYEING COMPOSITIONS

| EX-AMPLE | DEVELOPER OF FORMULA I | COUPLER | COLOR OBTAINED |
|---|---|---|---|
| 3 | 2,5-diamino-1-(3-pyridyl)-benzene*2HCl | 2-amino-4-(2-hydroxy-ethyl)amino anisole sulfate | dark blue |
| 4 | 2,5-diamino-1-(3-pyridyl)-benzene*2HCl | resorcinol | dark blond |
| 5 | 2,5-diamino-1-(3-pyridyl)-benzene*2HCl | m-aminophenol | dark gray |
| 6 | 2,5-diamino-1-(3-pyridyl)-benzene*2HCl | 5-amino-2-methyl-phenol | red |

Examples 7 to 50: Hair Dye Compositions

Hair Dye Solutions were prepared having the following composition:

| | | |
|---|---|---|
| 0.00125 mol | developer substance of formula I according to Table II | |
| 0.00125 mol | coupler substance according to Table II | |
| 0.01 g | potassium oleate (8% aqueous solution) | |
| 0.01 g | ammonia (22 percent aqueous solution) | |
| 0.01 g | ethanol | |
| 0.003 g | ascorbic acid | |
| to 1.0 g | water | |

1 g of the above-described dye solution were mixed immediately prior to use with 1 g of 6 percent hydrogen peroxide solution. Then the mixture was applied to bleached hair. After an acting time of 30 minutes at 40° C., the hair was rinsed with water, washed with a shampoo and dried. The resulting colors for the dyeing hair are summarized in the following Table II.

TABLE II

HAIR DYEING COMPOSITIONS

| EX-AMPLE | DEVELOPER OF FORMULA I | COUPLER | COLOR OBTAINED |
|---|---|---|---|
| 7 | 2,5-diamino-1-(6-methyl-2-pyridyl)benzene*3HCl | 1,3-diamino-4-(2-hydroxyethoxy)-benzene sulfate | dark blue |
| 8 | 2,5-diamino-1-(6-methyl-2-pyridyl)benzene*3HCl | 1-naphthol | blue |
| 9 | 2,5-diamino-1-(6-methyl-2-pyridyl)benzene*3HCl | 5-amino-2-methyl-phenol | red |
| 10 | 2,5-diamino-1-(6-methyl)-2-pyridyl)benzene*3HCl | resorcinol | dark blond |
| 11 | 2,5-diamino-1-(5-carbon-amido-3-pyridyl)benzene*3HCl | 1,3-diamino-4-(2-hydroxyethoxy)-benzene sulfate | dark blue |
| 12 | 2,5-diamino-1-(5-carbon-amido-3-pyridyl)benzene*3HCl | 1-naphthol | blue |
| 13 | 2,5-diamino-1-(5-carbon-amido-3-pyridyl)benzene*3HCl | 5-amino-2-methyl-phenol | red |
| 14 | 2,5-diamino-1-(5-carbon-amido-3-pyridyl)benzene*3HCl | resorcinol | dark blond |
| 15 | 2,5-diamino-1-(3-methyl-2-pyridyl)benzene*3HCl | 1,3-diamino-4-(2-hydroxyethoxy)-benzene sulfate | dark blue |
| 16 | 2,5-diamino-1-(3-methyl-2-pyridyl)benzene*3HCl | 1-naphthol | blue |
| 17 | 2,5-diamino-1-(3-methyl-2-pyridyl)benzene*3HCl | 5-amino-2-methyl-phenol | red |
| 18 | 2,5-diamino-1-(3-methyl)-2-pyridyl)benzene*3HCl | resorcinol | dark blond |
| 19 | 2,5-diamino-1-(3-trifluoro-methyl-2-pyridyl)benzene*3HCl | 1,3-diamino-4-(2-hydroxyethoxy)-benzene sulfate | dark blue |
| 20 | 2,5-diamino-1-(3-trifluoro-methyl-2-pyridyl)benzene*3HCl | 1-naphthol | blue |
| 21 | 2,5-diamino-1-(3-trifluoro-methyl-2-pyridyl)benzene*3HCl | 5-amino-2-methyl-phenol | red |
| 22 | 2,5-diamino-1-(3-trifluoro-methyl-2-pyridyl)benzene*3HCl | resorcinol | dark blond |
| 23 | 2,5-diamino-1-(2-pyridyl)-benzene*3HCl | 1,3-diamino-4-(2-hydroxyethoxy)-benzene sulfate | dark blue |
| 24 | 2,5-diamino-1-(2-pyridyl)-benzene*3HCl | 1-naphthol | blue |
| 25 | 2,5-diamino-1-(2-pyridyl)-benzene*3HCl | 5-amino-2-methyl-phenol | red |
| 26 | 2,5-diamino-1-(2-pyridyl)-benzene*3HCl | resorcinol | dark blond |
| 27 | 2,5-diamino-1-(5-cyano-3-pyridyl)benzene*3HCl | 1,3-diamino-4-(2-hydroxyethoxy)-benzene sulfate | dark blue |
| 28 | 2,5-diamino-1-(5-cyano-3-pyridyl)benzene*3HCl | 1-naphthol | blue |
| 29 | 2,5-diamino-1-(5-cyano-3-pyridyl)benzene*3HCl | 5-amino-2-methyl-phenol | red |
| 30 | 2,5-diamino-1-(5-cyano-3-pyridyl)benzene*3HCl | resorcinol | dark blond |
| 31 | 2,5-diamino-1-(5-methyl-2 pyridyl)benzene*3HCl | 1,3-diamino-4-(2-hydroxyethoxy)-benzene sulfate | dark blue |
| 32 | 2,5-diamino-1-(5-methyl-2-pyridyl)benzene*3HCl | 1-naphthol | blue |
| 33 | 2,5-diamino-1 -(5-methyl-2-pyridyl)benzene*3HCl | 5-amino-2-methyl-phenol | red |
| 34 | 2,5-diamino-1-(5-methyl)2-pyridyl)benzene*3HCl | resorcinol | dark blond |
| 35 | 2,5-diamino-1-(4-methyl-2-pyridyl)benzene*3HCl | 1,3-diamino-4-(2-hydroxyethoxy) benzene sulfate | dark blue |

TABLE II-continued

HAIR DYEING COMPOSITIONS

| EXAMPLE | DEVELOPER OF FORMULA I | COUPLER | COLOR OBTAINED |
|---|---|---|---|
| 36 | 2,5-diamino-1-(4-methyl-2-pyridyl)benzene*3HCl | 1-naphthol | blue |
| 37 | 2,5-diamino-1-(4-methyl-2-pyridyl)benzene*3HCl | 5-amino-2-methyl-phenol | red |
| 38 | 2,5-diamino-1-(4-methyl)-2-pyridyl)benzene*3HCl | resorcinol | dark blond |
| 39 | 2,5-diamino-1-(5-trifluoro-methyl-2-pyridyl)benzene*3HCl | 1,3-diamino-4-(2-hydroxyethoxy)-benzene sulfate | dark blue |
| 40 | 2,5-diamino-1-(5-trifluoro-methyl-2-pyridyl)benzene*3HCl | 1-naphthol | blue |
| 41 | 2,5-diamino-1-(5-trifluoro-2-pyridyl)benzene*3HCl | 5-amino-2-methyl-phenol | red |
| 42 | 2,5-diamino-1-(5-trifluoro-2-pyridyl)benzene*3HCl | resorcinol | dark blond |
| 43 | 2,5-diamino-1-(5-nitro-2-pyridyl)benzene*3HCl | 1,3-diamino-4-(2-hydroxyethoxy)-benzene sulfate | dark blue |
| 44 | 2,5-diamino-1-(5-nitro-2-pyridyl)benzene*3HCl | 1-naphthol | blue |
| 45 | 2,5-diamino-1-(5-nitro-2-pyridyl)benzene*3HCl | 5-amino-2-methyl-phenol | red |
| 46 | 2,5-diamino-1-(5-nitro-2-pyridyl)benzene*3HCl | resorcinol | dark blond |
| 47 | 2,5-diamino-1-(2-pyrimidyl)-benzene*3HCl | 1,3-diamino-4-(2-hydroxyethoxy)-benzene sulfate | dark blue |
| 48 | 2,5-diamino-1-(2-pyrimidyl)-benzene*3HCl | 1-naphthol | blue |
| 49 | 2,5-diamino-1-(2-pyrimidyl)-benzene*3HCl | 5-amino-2-methyl-phenol | red |
| 50 | 2,5-diamino-1-(2-pyrimidyl)-benzene*3HCl | resorcinol | dark blond |

Example 51: Hair Dye Composition

A hair dyeing solution having the following composition was prepared:

| | |
|---|---|
| 0.160 g | 2,5-diamino-1-(2-pyridyl)benzene*2HCl |
| 0.160 g | 1,4-diamino-2-(2-hydroxyethyl)benzene sulfate |
| 0.137 g | 1,3-dihydroxybenzene |
| 0.100 g | 1,3-dihydroxy-2-methylbenzene |
| 0.100 g | 2-amino-5-methylphenol |
| 10.000 g | potassium oleate (8 percent aqueous solution) |
| 10.000 g | ammonia (22 percent aqueous solution) |
| 10.000 g | isopropanol |
| 0.300 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a blond color.

Example 52: Hair Dye Composition

A hair dyeing solution having the following composition was prepared:

| | |
|---|---|
| 0.32 g | 2,5-diamino-1-(2-pyridyl)benzene*2HCl |
| 0.30 g | 5-amino-2-methylphenol |
| 0.60 g | 4-amino-3-methylphenol |
| 0.60 g | 4-aminophenol |
| 0.10 g | α-naphthol |
| 0.20 g | 2-chloro-6-(ethylamino)-4-nitrophenol |
| 10.00 g | potassium oleate (8 percent aqueous solution) |
| 10.00 g | ammonia (22 percent aqueous solution) |
| 10.00 g | isopropanol |
| 0.30 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a red color.

Example 53: Hair Dye Composition

A hair dyeing solution having the following composition was prepared:

| | |
|---|---|
| 0.32 g | 2,5-diamino-1-(2-pyridyl)benzene*2HCl |
| 0.04 g | 5-amino-2-methylphenol |
| 0.09 g | 2-amino-4-(2'-hydroxyethyl)amino-anisole sulfate |
| 0.03 g | 3-aminophenol |
| 0.03 g | 1,3-dihydroxybenzene |
| 0.04 g | 1,3-dihydroxy-2-methylbenzene |
| 0.10 g | 4-amino-3-methylphenol |
| 0.20 g | 2-amino-5-methylphenol |
| 0.10 g | 2-amino-6-methylphenol hydrochloride |
| 0.01 g | 4-chloro-N-(2-hydroxyethyl)-2-nitroaniline |
| 0.02 g | 2-amino-4,6-dinitrophenol |
| 0.10 g | 2-chloro-6-(ethylamino)-4-nitrophenol |
| 10.00 g | potassium oleate (8 percent aqueous solution) |
| 10.00 g | ammonia (22 percent aqueous solution) |
| 10.00 g | isopropanol |
| 0.30 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Example 54: Hair Dye Composition

A hair dyeing solution having the following composition was prepared:

| | |
|---|---|
| 0.32 g | 2,5-diamino-1-(2-pyridyl)benzene*2HCl |
| 0.04 g | 5-amino-2-methylphenol |
| 0.05 g | 1,3-diamino-4-(2-hydroxyethoxy)benzene*sulfate |
| 0.03 g | 3-aminophenol |
| 0.03 g | 1,3-dihydroxybenzene |

-continued

| | |
|---|---|
| 0.04 g | 1,3-dihydroxy-2-methylbenzene |
| 0.10 g | 4-amino-3-methylphenol |
| 0.20 g | 2-amino-5-methylphenol |
| 0.10 g | 2-amino-6-methylphenol hydrochloride |
| 0.01 g | 4-chloro-N-(2-hydroxyethyl)-2-nitroaniline |
| 0.02 g | 2-amino-4,6-dinitrophenol |
| 0.10 g | 2-chloro-6-(ethylamino)4-nitrophenol |
| 10.00 g | potassium oleate (8 percent aqueous solution) |
| 10.00 g | ammonia (22 percent aqueous solution) |
| 10.00 g | isopropanol |
| 0.30 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Example 55: Hair Dye Composition

A hair dyeing solution having the following composition was prepared:

| | |
|---|---|
| 0.220 g | 2,5-diamino-1-(2-pyridyl)benzene*2HCl |
| 0.100 g | 1,4-diamino-2-(2-hydroxyethyl)benzene sulfate |
| 0.020 g | 5-amino-2-methylphenol |
| 0.010 g | 1,3-diamino4-(2-hydroxyethoxy)benzene sulfate |
| 0.004 g | 2-amino-4-(2'-hydroxyethyl)amino anisole sulfate |
| 0.020 g | 1,3-dihydroxybenzene |
| 0.040 g | 1,3-dihydroxy-2-methylbenzene |
| 0.008 g | 4-amino-3-methylphenol |
| 10.000 g | potassium oleate (8 percent aqueous solution) |
| 10.000 g | ammonia (22 percent aqueous solution) |
| 10.000 g | isopropanol |
| 0.300 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Example 56: Hair Dye Composition

A hair dyeing solution having the following composition was prepared:

| | |
|---|---|
| 0.220 g | 2,5-diamino-1-(2-pyridyl)benzene*2HCl |
| 0.100 g | 4-di(2-hydroxyethyl)amino-aniline sulfate |
| 0.020 g | 5-amino-2-methylphenol |
| 0.010 g | 1,3-diamino-4-(2-hydroxyethoxy)benzene*sulfate |
| 0.015 g | 2-amino-4-(2'-hydroxyethyl)aminoanisole sulfate |
| 0.020 g | 1,3-dihydroxybenzene |
| 0.040 g | 1,3-dihydroxy-2-methylbenzene |
| 0.008 g | 4,5-diamino-1-(2-hydoxyethyl)-1H-pyrazole sulfate |
| 10.000 g | potassium oleate (8 percent aqueous solution) |
| 10.000 g | ammonia (22 percent aqueous solution) |
| 10.000 g | isopropanol |
| 0.300 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Example 57: Hair Dye Composition

A hair dyeing solution having the following composition was prepared:

| | |
|---|---|
| 0.320 g | 2,5-diamino-1-(2-pyridyl)benzene*2HCl |
| 0.020 g | 5-amino-2-methylphenol |
| 0.010 g | 1,3-diamino-4-(2-hydroxyethoxy)benzene*sulfate |
| 0.015 g | 2-amino-4-(21-hydroxyethyl)amino anisole sulfate |
| 0.020 g | 1,3-dihydroxybenzene |
| 0.040 g | 1,3-dihydroxy-2-methylbenzene |
| 0.008 g | 4-amino-2-(aminomethyl)phenol dihydrochloride |
| 10.000 g | potassium oleate (8 percent aqueous solution) |
| 10.000 g | ammonia (22 percent aqueous solution) |
| 10.000 g | isopropanol |
| 0.300 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Example 58: Hair Dye Composition

A hair dyeing solution having the following composition was prepared:

| | |
|---|---|
| 0.600 g | 2,5-diamino-1-(2-pyridyl)benzene*2HCl |
| 0.137 g | 1,3-dihydroxybenzene |
| 0.150 g | 1-chloro-2,4-dihydroxybenzene |
| 0.100 g | 3-aminophenol |
| 10.000 g | potassium oleate (8 percent aqueous solution) |
| 10.000 g | ammonia (22 percent aqueous solution) |
| 10.000 g | ethanol |
| 0.300 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a medium blond color.

Example 59: Hair Dye Composition

A hair dyeing solution having the following composition was prepared:

| | |
|---|---|
| 0.600 g | 2,5-diamino-1-(3-methyl-2-pyridyl)benzene*2HCl |
| 0.137 g | 1,3-dihydroxybenzene |
| 0.150 g | 1-chloro-2,4-dihydroxybenzene |
| 0.100 g | 5-amino-2-methylphenol |
| 10.000 g | potassium oleate (8 percent aqueous solution) |
| 10.000 g | ammonia (22 percent aqueous solution) |

-continued

| | |
|---|---|
| 10.000 g | ethanol |
| 0.300 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a medium blond color.

Example 60: Hair Dye Composition

A hair dyeing solution having the following composition was prepared:

| | |
|---|---|
| 0.40 g | 2,5-diamino-1-(2-pyridyl)benzene*2HCl |
| 0.20 g | 1-chloro-2,4-dihydroxybenzene |
| 0.05 g | 3-aminophenol |
| 0.09 g | 1,3-diamino-4-(2-hydroxyethoxy)benzene*sulfate |
| 10.000 g | potassium oleate (8 percent aqueous solution) |
| 10.000 g | ammonia (22 percent aqueous solution) |
| 10.000 g | ethanol |
| 0.300 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a blond color.

Example 61: Hair Dye Composition

A hair dyeing solution having the following composition was prepared:

| | |
|---|---|
| 0.40 g | 2,5-diamino-1-(3-methyl-2-pyridyl)benzene*2HCl |
| 0.20 g | 1-chloro-2,4-dihydroxybenzene |
| 0.05 g | 2-amino-5-methylphenol |
| 10.00 g | potassium oleate (8 percent aqueous solution) |
| 10.00 g | ammonia (22 percent aqueous solution) |
| 10.00 g | ethanol |
| 0.30 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a blond color.

Example 62: Hair Dye Composition

A hair dyeing solution having the following composition was prepared:

| | |
|---|---|
| 0.52 g | 2,5-diamino-1-(2-pyridyl)benzene*2HCl |
| 0.70 g | 5-hydroxy-1,3-benzodioxole |
| 0.05 g | 3-aminophenol |
| 15.00 g | cetyl alcohol |
| 3.00 g | ammonia (22 percent aqueous solution) |
| 3.50 g | sodium lauryl alcohol-diglycol ether sulfate (28 percent aqueous solution) |
| 0.30 g | sodium sulfite, water-free |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a blond color.

Example 63: Hair Dye Composition

A hair dyeing solution having the following composition was prepared:

| | |
|---|---|
| 0.52 g | 2,5-diamino-1-(3-methyl-2-pyridyl)benzene*2HCl |
| 0.70 g | 5-hydroxy-1,3-benzodioxole |
| 0.05 g | 3-amino-2-chloro-6-methylphenol |
| 15.00 g | cetyl alcohol |
| 3.00 g | ammonia (22 percent aqueous solution) |
| 3.50 g | sodium lauyl alcohol-diglycol ether sulfate (28 percent aqueous solution) |
| 0.30 g | sodium, sulfite, water-free |
| ad water to 100g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a medium blond color.

Example 64: Hair Dye Composition

A hair dyeing solution having the following composition was prepared:

| | |
|---|---|
| 0.40 g | 2,5-diamino-1-(2-pyridyl)benzene*2HCl |
| 0.20 g | 5-((2-hydroxyethyl)amino-1,3-benzodioxole*hydrochloride |
| 0.05 g | 3-aminophenol |
| 0.10 g | 3-amino-2-chloro-6-methylphenol |
| 10.00 g | potassium oleate (8 percent aqueous solution) |
| 10.00 g | ammonia (22 percent aqueous solution) |
| 10.00 g | ethanol |
| 0.39 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a blond color.

Example 65: Hair Dye Composition

A hair dyeing solution having the following composition was prepared:

| | |
|---|---|
| 0.40 g | 2,5-diamino-1-(3-methyl-2-pyridyl)benzene*2HCl |
| 0.20 g | 5-((2-hydroxyethyl)amino)-1,3-benzodioxole*HCl |
| 0.05 g | 5-amino-2-methylphenol |
| 0.10 g | 3-amino-2-chloro-6-methylphenol |
| 10.00 g | potassium oleate (8 percent aqueous solution) |
| 10.00 g | ammonia (22 percent aqueous solution) |
| 10.00 g | ethanol |
| 0.30 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a blond color.

Example 66: Hair Dye Composition

A hair dyeing solution having the following composition was prepared:

| | |
|---|---|
| 1.02 g | 2,5-diamino-1-(2-pyridyl)benzene*2HCl |
| 0.50 g | 1,3-dihydroxybenzene |
| 0.09 g | 3-aminophenol |
| 0.01 g | 24-diamino-1-fluoro-5-methylbenzene sulfate |
| 15.00 g | cetyl alcohol |
| 3.00 g | ammonia (22 percent aqueous solution) |
| 3.50 g | sodium lauryl alcohol-diglycol ether sulfate (28 percent aqueous solution) |
| 0.30 g | sodium sulfite, water-free |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Example 67: Hair Dye Composition

A hair dyeing solution having the following composition was prepared:

| | |
|---|---|
| 1.02 g | 2,5-diamino-1-(3-methyl-2-pyridyl)benzene*2HCl |
| 0.50 g | 1,3-dihydroxy-2-methylbenzene |
| 0.09 g | 5-amino-2-methylphenol |
| 0.01 g | 2,4-diamino-1-fluoro-5-methylbenzene sulfate |
| 15.00 g | cetyl alcohol |
| 3.00 g | ammonia (22 percent aqueous solution) |
| 3.00 g | sodium lauryl alcohol-diglycol ether sulfate (28 percent aqueous solution) |
| 0.30 g | sodium sulfite, water-free |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Example 68: Hair Dye Composition

A hair dyeing solution having the following composition was prepared:

| | |
|---|---|
| 0.62 g | 2,5-diamino-1-(2-pyridyl)benzene *2HCl |
| 0.15 g | 3-amino-6-methoxy-2-(methylamino)-pyridine*2HCl |
| 0.05 g | 1,3-diamino-4-(2-hydroxyethoxy)benzene*HCl |
| 0.30 g | 1,3-dihydroxybenzene |
| 0.10 g | 4-amino-5-methylphenol |
| 10.00 g | potassium oleate (8 percent aqueous solution) |
| 10.00 g | ammonia (22 percent aqueous solution) |
| 10.00 g | isopropanol |
| 0.30 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a red-brown color.

Example 69: Hair Dye Composition

A hair dyeing solution having the following composition was prepared:

| | |
|---|---|
| 0.62 g | 2,5-diamino-1-(3-methyl-2-pyridyl)benzene*2HCl |
| 0.05 g | 3-amino-6-methoxy-2-(methylamino)-pyridine*2HCl |
| 0.30 g | 1-chloro-2,4-dihydroxybenzene |
| 0.10 g | 3-aminophenol |
| 10.00 g | potassium oleate (8 percent aqueous solution) |
| 10.00 g | ammonia (22 percent aqueous solution) |
| 10.00 g | isopropanol |
| 0.30 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a red-brown color.

Example 70: Hair Dye Composition

A hair dyeing solution having the following composition was prepared:

| | |
|---|---|
| 0.50 g | 2,5-diamino-1-(3-methyl-2-pyridyl)benzene*2HCl |
| 0.20 g | 5-methyl-2-(1-methylethyl)phenol |
| 0.30 g | 1,3-dihydroxybenzene |
| 0.05 g | 4-amino-5-methylphenol |
| 10.00 g | potassium oleate (8 percent aqueous solution) |
| 10.00 g | ammonia (22 percent aqueous solution) |
| 10.00 g | isopropanol |
| 0.30 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a blond color.

Example 71: Hair Dye Composition

A hair dyeing solution having the following composition was prepared:

| | |
|---|---|
| 0.62 g | 2,5-diamino-1-(2-pyridyl)benzene*2HCl |
| 0.06 g | 5-methyl-2-(1-methylethyl)phenol |
| 0.30 g | 1,3-dihydroxybenzene |
| 0.15 g | 1,3-dihydroxy-2-methylbenzene |
| 10.00 g | potassium oleate (8 percent aqueous solution) |
| 10.00 g | ammonia (22 percent aqueous solution) |
| 10.00 g | isopropanol |
| 0.30 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a blond color.

Example 72: Hair Dye Composition

A hair dyeing solution having the following composition was prepared:

| | |
|---|---|
| 3.02 g | 2,5-diamino-1-(3-methyl-2-pyridyl)benzene*2HCl |
| 1.50 g | 1,3-dihydroxybenzene |
| 1.50 g | 1,3-diamino-4-(2-hydroxyethoxy)benzene*sulfate |
| 0.30 g | 3-aminophenol |
| 15.00 g | cetyl alcohol |
| 3.00 g | ammonia (22 percent aqueous solution) |
| 3.50 g | sodium lauryl alcohol-diglycol ether sulfate (28 percent aqueous solution) |
| 0.30 g | sodium sulfite, water-free |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a black color.

Example 73: Hair Dye Composition

A hair dyeing solution having the following composition was prepared:

| | |
|---|---|
| 3.02 g | 2,5-diamino-1-(2-pyridyl)benzene*2HCl |
| 1.50 g | 1,3-dihydroxybenzene |
| 1.50 g | 5-((2-hydroxyethyl)amino)-2-methoxyaniline*sulfate |
| 0.30 g | 3-aminophenol |
| 15.00 g | cetyl alcohol |
| 3.00 g | ammonia (22 percent aqueoussolution) |
| 3.50 g | sodium lauryl alcohol-diglycol ether sulfate (28 percent aqueous solution) |
| 0.30 g | sodium sulfite, water-free |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a black color.

Example 74: Hair Dye Composition

A hair dyeing solution having the following composition was prepared:

| | |
|---|---|
| 0.30 g | 2,5-diamino-1-(3-methyl-2-pyridyl)benzene*2HCl |
| 0.18 g | 1-chloro-2,4-dihydroxybenzene |
| 0.30 g | 4,5-diamino-1-(2'-hydroxyethyl)-1H-pyrazole*sulfate |
| 0.30 g | 1-naphthol |
| 10.00 g | potassium oleate (8 percent aqueous solution) |
| 10.00 g | ammonia (22 percent aqueous solution) |
| 10.00 g | isopropanol |
| 0.30 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a red-brown color.

Example 75: Hair Dye Composition

A hair dyeing solution having the following composition was prepared:

| | |
|---|---|
| 0.30 g | 2,5-diamino-1-(2-pyridyl)benzene*2HCl |
| 0.18 g | 1,3-dihydroxy-2-methylbenzene |
| 0.30 g | 4-amino-2-(aminomethyl)phenol hydrochloride |
| 0.30 g | 1-naphthol |
| 10.00 g | potassium oleate (8 percent aqueous solution) |
| 10.00 g | ammonia (22 percent aqueous solution) |
| 10.00 g | isopropanol |
| 0.30 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a red-brown color.

Example 76: Hair Dye Composition

A hair dyeing solution having the following composition was prepared:

| | |
|---|---|
| 0.30 g | 2,5-diamino-1-(3-methyl-2-pyridyl)benzene*2HCl |
| 0.18 g | 1,3-dihydroxybenzene |
| 0.30 g | 4,5-diamino-1-(2'-hydroxyethyl)-1H-pyrazole*sulfate |
| 0.30 g | acetic acid-(methylnaphthalen-1-yl)-ester |
| 10.0 g | potassium oleate (8 percent aqueous solution) |
| 10.0 g | ammonia (22 percent aqueous solution) |
| 10.0 g | isopropanol |
| 0.3 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a red-brown color.

Example 77: Hair Dye Composition

A hair dyeing solution having the following composition was prepared:

| | |
|---|---|
| 0.30 g | 2,5-diamino-1-(2-pyridyl)benzene*2HCl |
| 0.18 g | 1,3-dihydroxybenzene |
| 0.30 g | 4-amino-3-methylphenol |
| 0.30 g | acetic acid-(methylnaphthalen-1-yl)-ester |
| 10.0 g | potassium oleate (8 percent aqueous solution) |
| 10.0 g | ammonia (22 percent aqueous solution) |
| 10.0 g | isopropanol |
| 0.3 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a red-brown color.

Example 78: Hair Dye Composition

A hair dyeing solution having the following composition was prepared:

| | |
|---|---|
| 1.30 g | 2,5-diamino-1-(3-methyl-2-pyridyl)benzene*2HCl |
| 0.08 g | 5-amino-2-methylphenol |
| 0.05 g | 1,3-diamino-4-(2-hydroxyethoxy)benzene*sulfate |
| 0.01 g | 3-aminophenol |
| 0.50 g | 1,3-dihydroxybenzene |
| 0.10 g | 4-amino-5-methylphenol |
| 0.02 g | 2-amino-5-methylphenol |
| 0.02 g | 2-amino-6-chloro-4-nitrophenol hydrochloride |
| 10.00 g | potassium oleate (8 percent aqueous solution) |
| 10.00 g | ammonia (22 percent aqueous solution) |
| 10.00 g | isopropanol |
| 0.30 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Example 79: Hair Dye Composition

A hair dyeing solution having the following composition was prepared:

| | |
|---|---|
| 0.60 g | 2,5-diamino-1-(2-pyridyl)benzene*2HCl |
| 0.30 g | 1,3-dihydroxybenzene |
| 0.01 g | 2-amino-5-methylphenol |
| 0.10 g | 3-amino-2-chloro-methylphenol |
| 0.05 g | 2-chloro-6-(ethylamino)-4-nitrophenol |
| 10.00 g | potassium oleate (8 percent aqueous solution) |
| 10.00 g | ammonia (22 percent aqueous solution) |
| 10.00 g | ethanol |
| 0.30 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a blond color.

Example 80: Hair Dye Composition

A hair dyeing solution having the following composition was prepared:

| | |
|---|---|
| 0.90 g | 2,5-diamino-1-(3-methyl-2-pyridyl)benzene*2HCl |
| 0.40 g | 1,3-dihydroxybenzene |
| 0.01 g | 2-amino-5-methylphenol |
| 0.10 g | 3-aminophenol |
| 0.02 g | 2-amino-6-chloro-4-nitrophenol hydrochloride |
| 0.01 g | 2-amino-4,6-dinitrophenol |
| 10.00 g | potassium oleate (8 percent aqueous solution) |
| 10.00 g | ammonia (22 percent aqueous solution) |
| 10.00 g | ethanol |
| 0.30 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Example 81: Hair Dye Composition

A hair dyeing solution having the following composition was prepared:

| | |
|---|---|
| 0.90 g | 2,5-diamino-1-(2-pyridyl)benzene*2HCl |
| 0.40 g | 1,3-dihydroxybenzene |
| 0.40 g | 1,3-dihydroxy-2-methylbenzene |
| 0.10 g | 5-amino-2-methylphenol |
| 0.05 g | 3-amino-2-chloro-6-methylphenol |
| 0.40 g | 1,4-diamino-2-hydroxyethylbenzene*sulfate |
| 0.05 g | 4-amino-3-methylphenol hydrochloride |

-continued

| | |
|---|---|
| 0.01 g | 2-amino-4,6-dinitrophenol |
| 0.07 g | 2-chloro-6-(ethylamino)-4-nitrophenol |
| 10.00 g | potassium oleate (8 percent aqueous solution) |
| 10.00 g | ammonia (22 percent aqueous solution) |
| 10.00 g | ethanol |
| 0.30 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Example 82: Hair Dye Composition

A hair dyeing solution having the following composition was prepared:

| | |
|---|---|
| 0.90 g | 2,5-diamino-1-(2-pyridyl)benzene*2HCl |
| 0.50 g | 2,5-diamino-1-methylbenzene sulfate |
| 0.40 g | 1,3-dihydroxybenzene |
| 0.40 g | 4-amino-3-methylphenol |
| 0.10 g | 5-amino-2-methylphenol |
| 0.10 g | 5-((2-hydroxyethyl)amino-2-methoxyaniline sulfate |
| 0.10 g | 3-aminophenol |
| 0.05 g | 1,3-diamino-4-(2-hydroxyethoxy)benzene*sulfate |
| 0.07 g | 2-amino-6-chloro-4-nitrophenol hydrochloride |
| 10.00 g | potassium oleate (8 percent aqueous solution) |
| 10.00 g | ammonia (22 percent aqueous solution) |
| 10.00 g | ethanol |
| 0.30 g | ascorbic acid |
| ad water to 100 g | |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Unless otherwise indicated, all percentages are percentages by weight.

The disclosure in German Patent Application 199 22 392.0 of May 14, 1999 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in new diaminobenzene derivative compounds and dye compositions containing same, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

We claim:
1. A p-diaminobenzene derivative compound of formula I, or a phyiologically compatible water-soluble salt thereof:

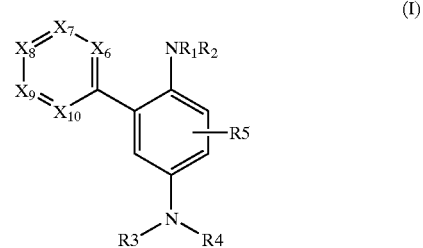

(I)

wherein $X_6$, $X_7$, $X_8$, $X_9$, $X_{10}$, each, independently of each other, represents nitrogen or C—R6, C—R7, C—R8, C—R9, C—R10, with the proviso that at least one and at most three of the groups, $X_6$, $X_7$, $X_8$, $X_9$, $X_{10}$, represent nitrogen and R6, R7, R8, R9, $R_{10}$ each, independently of each other, represents hydrogen, a halogen atom, a cyano group, a hydroxy group, a $C_1$- to $C_4$-alkoxy group, a $C_1$- to $C_6$-alkyl group, a $C_1$- to $C_4$-alkylthioether group, a mercapto group, a nitro group, an amino group, a $C_1$- to $C_4$-alkylamino group, a di($C_1$- to $C_4$-)alkylamino group, a trifluoromethane group, a —C(O)H group, a —C(O)CH$_3$ group, a —C(O)CF$_3$ group, a —Si(CH$_3$)$_3$ group, a —C(O)NH$_2$ group, a $C_1$- to $C_4$-hydroxyalkyl group, a $C_3$- to $C_4$-dihydroxyalkyl group, a —CH=CHR11 group, a —(CH$_2$)$_p$—CO$_2$R12 group or a —(CH$_2$)$_p$R13 group with p=1, 2, 3 or 4, a —C(R14)=NR15 group or a —C(R17)H—NR18R19 group;

R1, R2, R3 and R4 each, independently of each other, represents hydrogen, a $C_1$- to $C_6$-alkyl group, a $C_1$- to $C_4$-hydroxyalkyl group, a $C_2$- to $C_4$-dihydroxyalkyl group or a $C_1$- to $C_4$-alkoxy-($C_1$- to $C_4$)-alkyl group or R1 and R2 or R3 and R4 represent a four-membered to eight-membered aliphatic ring, with the proviso that at least two of the R1 to R4 groups represent hydrogen;

R5 represents hydrogen, a hydroxy group, a halogen atom, a $C_1$- to $C_4$-alkyl group, a $C_1$- to $C_4$-hydroxyalkyl group or a $C_1$- to $C_4$-alkoxy group;

R11 represents hydrogen, a hydroxy group, an amino group, a —CO$_2$R12 or a —C(O)CH$_3$ group;

R12, R14 and R17 each, independently of each other, represents hydrogen or a $C_1$- to $C_4$-alkyl group;

R13 represents an amino group or a nitrile group;

R15, R18 and R19 each, independently of each other, represents hydrogen, a hydroxy group, a $C_1$- to $C_4$-alkyl group, a $C_1$- to $C_4$-hydroxyalkyl group, a $C_3$- to $C_4$-dihydroxyalkyl group or a group of the formula:

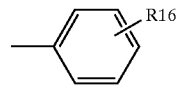

and
wherein R16 represents hydrogen, an amino group or a hydroxy group.

2. A p-diaminobenzene derivative compound selected from the group consisting of 2,5-diamino-1-(2-pyridyl)benzene; 2,5-diamino-1-(3-pyridyl)benzene; 2,5-diamino-1-(4-pyridyl)-benzene; 2,5-diamino-4-methoxy-1-(2-pyridyl)benzene; 2,5-diamino-4-methoxy-1-(3-pyridyl)benzene;

2,5-diamino-4-methoxy-1-(4-pyridyl)benzene; 2,5-diamino4-methyl-1-(2-pyridyl)benzene; 2,5-diamino-4-methyl-1-(3-pyridyl)benzene; 2,5-diamino-4-methyl-1-(4-pyridyl)benzene; 2,5-diamino-1-(3-amino-2-pyridyl)-benzene; 2,5-diamino-1-(3-chloro-2-pyridyl)benzene; 2,5-diamino-1-(3-fluoro-2-pyridyl)benzene; 2,5-diamino-1-(3-hydroxy-2-pyridyl)benzene; 2,5-diamino-1-(3-methyl-2-pyridyl)benzene; 2,5-diamino-1-(3-trifluoromethyl-2-pyridyl)benzene; 2,5-diamino-1-(4-amino-2-pyridyl)benzene; 2,5-diamino-1-(4-chloro-2-pyridyl)-benzene; 2,5-diamino-1-(4-fluoro-2-pyridyl)benzene; 2,5-diamino-1-(4-hydroxy-2-pyridyl)benzene; 2,5-diamino-1-(4-methyl-2-pyridyl)benzene; 2,5-diamino-1-(4-trifluoromethyl-2-pyridyl)benzene; 2,5-diamino-1-(5-amino-2-pyridyl)benzene; 2,5-diamino-1-(5-chloro-2-pyridyl)benzene; 2,5-diamino-1-(5-fluoro-2-pyridyl)-benzene; 2,5-diamino-1-(5-hydroxy-2-pyridyl)benzene; 2,5-diamino-1-(5-methyl-2-pyridyl)benzene; 2,5-diamino-1-(5-trifluoromethyl-2-pyridyl)benzene; 2,5-diamino-1-(6-amino-2-pyridyl)benzene; 2,5-diamino-1-(6-chloro-2-pyridyl)-benzene; 2,5-diamino-1-(6-fluoro-2-pyridyl)benzene; 2,5-diamino-1-(6-hydroxy-2-pyridyl)benzene; 2,5-diamino-1-(6-methyl-2-pyridyl)benzene; 2,5-diamino-1-(6-trifluoromethyl-2-pyridyl)benzene; 2,5-diamino-1-(2-amino-3-pyridyl)-benzene; 2,5-diamino-1-(2-chloro-3-pyridyl)benzene; 2,5-diamino-1-(2-fluoro-3-pyridyl)benzene; 2,5-diamino-1-(2-hydroxy- 3-pyridyl)benzene; 2,5-diamino-1-(2-methyl-3-pyridyl)benzene; 2,5-diamino-1-(2-trifluoromethyl-3-pyridyl)-benzene; 2,5-diamino-1-(4-amino-3-pyridyl)benzene; 2,5-diamino-1-(4-chloro-3-pyridyl)benzene; 2,5-diamino-1-(4-fluoro-3-pyridyl)benzene; 2,5-diamino-1-(4-hydroxy-3-pyridyl)benzene; 2,5-diamino-1-(4-methyl-3-pyridyl)benzene; 2,5-diamino-1-(4-trifluoromethyl-3-pyridyl)benzene; 2,5-diamino-1-(5-amino-3-pyridyl)benzene; 2,5-diamino-1-(5-chloro-3-pyridyl)benzene; 2,5-diamino-1-(5-fluoro-3-pyridyl)benzene; 2,5-diamino-1-(5-hydroxy-3-pyridyl)benzene; 2,5-diamino-1-(5-methyl-3-pyridyl)benzene; 2,5-diamino-1-(5-trifluoromethyl-3-pyridyl)benzene; 2,5-diamino-1-(6-amino-3-pyridyl)benzene; 2,5-diamino-1-(6-chloro-3-pyridyl)benzene; 2,5-diamino-1-(6-fluoro-3-pyridyl)benzene; 2,5-diamino-1-(6-hydroxy-3-pyridyl)benzene; 2,5-diamino-1-(6-methyl-3-pyridyl)-benzene; 2,5-diamino-1-(6-trifluoromethyl-3-pyridyl)benzene; 2,5-diamino-1-(2-amino-4-pyridyl)benzene; 2,5-diamino-1-(2-chloro-4-pyridyl)benzene; 2,5-diamino-1-(2-fluoro-4-pyridyl)benzene; 2,5-diamino-1-(2-hydroxy4-pyridyl)-benzene; 2,5-diamino-1-(2-methyl-4-pyridyl)benzene; 2,5-diamino-1-(2-trifluoro-methyl-4-pyridyl)benzene; 2,5-diamino-1-(3-amino4-pyridyl)benzene; 2,5-diamino-1-(3-chloro-4-pyridyl)benzene; 2,5-diamino-1-(3-fluoro4-pyridyl)-benzene; 2,5-diamino-1-(3-hydroxy-4-pyridyl)benzene; 2,5-diamino-1-(3-methyl4-pyridyl)benzene; 2,5-diamino-1-(3-trifluoromethyl-4-pyridyl)benzene; 2,5-diamino-1-(5-amino-4-pyridyl)benzene; 2,5-diamino-1-(5-chloro-4-pyridyl)-benzene; 2,5-diamino-1-(5-fluoro-4-pyridyl)benzene; 2,5-diamino-1-(5-hydroxy-4-pyridyl)benzene; 2,5-diamino-1-(5-methyl-4-pyridyl)benzene; 2,5-diamino-1-(5-trifluoromethyl-4-pyridyl)benzene; 2,5-diamino- 1-(6-amino-4-pyridyl)benzene; 2,5-diamino-1-(6-chloro-4-pyridyl)benzene; 2,5-diamino-1-(6-fluoro-4-pyridyl)-benzene; 2,5-diamino-1-(6-hydroxy-4-pyridyl)benzene; 2,5-diamino-1-(6-methyl-4-pyridyl)benzene; 2,5-diamino-1-(6-trifluoromethyl-4-pyridyl)benzene; 2,5-diamino-1-(2-pyrimidyl)benzene; 2,5-diamino-1-(4-pyrimidyl)benzene; 2,5-diamino-1-(5-pyrimidyl)benzene; 2,5-diamino-1-(6-pyrimidyl)benzene; 2-hydroxyethylamino-5-amino-1-(2-pyridyl)benzene; 2-hydroxyethylamino-5-amino-1-(2-pyridyl)benzene; 2-hydroxyethylamino-5-amino-1-(3-pyridyl)-benzene; 2-hydroxyethylamino-5-amino-1-(4-pyridyl)benzene; 2-bis-(hydroxy-ethyl)amino-5-amino-1-(2-pyridyl)benzene; 2-bis-(hydroxyethyl)amino-5-amino-1-(3-pyridyl)benzene; 2-bis-(hydroxyethyl)amino-5-amino-1-(4-pyridyl)benzene; 2,5-diamino-1-(3-cyano-2-pyridyl)benzene; 2,5-diamino-1-(3-nitro-2-pyridyl)-benzene; 2,5-diamino-1-(4-cyano-2-pyridyl)benzene; 2,5-diamino-1-(4-nitro-2-pyridyl)benzene; 2,5-diamino-1-(5-cyano-2-pyridyl)benzene; 2,5-diamino-1-(5-nitro-2-pyridyl)benzene; 2,5-diamino-1-(6-cyano-2-pyridyl)benzene; 2,5-diamino-1-(6-nitro-2-pyridyl)benzene; 2,5-diamino-1-(2-cyano-4-pyridyl)benzene; 2,5-diamino-1-(2-nitro-4-pyridyl)benzene; 2,5-diamino-1-(3-cyano-4-pyridyl)benzene; 2,5-diamino-1-(3-nitro-4-pyridyl)benzene; 2,5-diamino-1-(5-cyano-4-pyridyl)-benzene; 2,5-diamino-1-(5-nitro-4-pyridyl)benzene; 2,5-diamino-1-(6-cyano-4-pyridyl)benzene; 2,5-diamino-1-(6-nitro-4-pyridyl)benzene; 2,5-diamino-1-(2-cyano-4-pyridyl)benzene; 2,5-diamino-1-(2-nitro-3-pyridyl)benzene; 2,5-diamino-1-(4-cyano-3-pyridyl)benzene; 2,5-diamino-1-(4-nitro-3-pyridyl)benzene; 2,5-diamino-1-(5-cyano-3-pyridyl)benzene; 2,5-diamino-1-(5-nitro-3-pyridyl)benzene; 2,5-diamino-1-(6-cyano-3-pyridyl)benzene 2,5-diamino-1-(6-cyano-3-pyridyl)benzene and 2,5-diamino-1-(6-nitro-3-pyridyl)benzene; or a physiologically compatible salt thereof.

3. A p-diaminobenzene derivative compound selected from the group consisting of 2,5-diamino-1-(2-pyridyl)benzene; 2,5-diamino-1-(3-pyridyl)benzene; 2,5-diamino-1-(4-pyridyl)benzene; 2,5-diamino-1-(2-pyrimidyl)benzene; 2,5-diamino-1-(6-methyl-2-pyridyl)benzene; 2,5-diamino-1-(4-methyl-2-pyridyl)-benzene; 2,5-diamino-1-(5-methyl-2-pyridyl)benzene and 2,5-diamino-1-(3-methyl-2-pyridyl)benzene; or a physiologically compatible salt thereof.

4. A composition for oxidative dyeing of keratin fibers, said composition containing at least one coupler substance and at least one developer substance, wherein said at least one developer substance comprises a p-diaminobenzene derivative compound of formula I, or a phyiologically compatible water-soluble salt thereof:

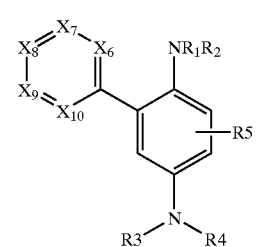

(I)

wherein $X_6$, $X_7$, $X_8$, $X_9$, $X_{10}$, each, independently of each other, represents nitrogen or C—R6, C—R7, C—R8, C—R9, C—R10, with the proviso that at least one and at most three of the groups, $X_6$, $X_7$, $X_8$, $X_9$, $X_{10}$, represent nitrogen and R6, R7, R8, R9, R10 each, independently of each other, represents hydrogen, a halogen atom, a cyano group, a hydroxy group, a $C_1$- to $C_4$-alkoxy group, a $C_1$- to $C_6$-alkyl group, a $C_1$- to $C_4$-alkylthioether group, a mercapto group, a nitro group, an amino group, a $C_1$- to $C_4$-alkylamino group, a di($C_1$- to $C_4$-)alkylamino group, a trifluoromethane group, a —C(O)H group, a —C(O)CH$_3$ group, a —C(O)CF$_3$ group, a —Si(CH$_3$)$_3$ group, a —C(O)NH$_2$ group, a $C_1$- to C4-hydroxyalkyl group, a $C_3$- to $C_4$-dihydroxyalkyl group, a —CH=CHR11 group, a —(CH$_2$)$_p$—CO$_2$R12 group or a —(CH$_2$)$_p$R13 group with p=1, 2, 3 or 4, a —C(R14)=NR15 group or a —C(R17)H—NR18R19 group;

R1, R2, R3 and R4 each, independently of each other, represents hydrogen, a C$_1$- to C$_6$-alkyl group, a C$_1$- to C$_4$-hydroxyalkyl group, a C$_2$- to C4-dihydroxyalkyl group or a C$_1$- to C$_4$-alkoxy-(C$_1$- to C$_4$)-alkyl group or R1 and R2 or R3 and R4 represent a four-membered to eight-membered aliphatic ring, with the proviso that at least 2 of the R1 to R4 groups represent hydrogen;

R5 represents hydrogen, a hydroxy group, a halogen atom, a C$_1$- to C4-alkyl group, a C$_1$- to C$_4$-hydroxyalkyl group or a C$_1$- to C$_4$-alkoxy group;

R11 represents hydrogen, a hydroxy group, an amino group, a —CO$_2$R12 or a —C(O)CH$_3$ group;

R12, R14 and R17 each, independently of each other, represents hydrogen or a C$_1$- to C$_4$-alkyl group;

R13 represents an amino group or a nitrile group;

R15, R18 and R19 each, independently of each other, represents hydrogen, a hydroxy group, a C$_1$- to C$_4$-alkyl group, a C$_1$- to C$_4$-hydroxyalkyl group, a C$_3$- to C$_4$-dihydroxyalkyl group or a group of the formula:

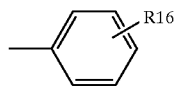

and wherein R16 represents hydrogen, an amino group or a hydroxy group.

5. The composition as defined in claim 4, containing from 0.005 to 20 percent by weight of said p-diaminobenzene derivative compound of formula I.

6. The composition as defined in claim 4, containing from 0.005 to 20 percent by weight of said at least one coupler substance and from 0.005 to 20 percent by weight of said at least one developer substances, based on a total amount of said composition.

7. The composition as defined in claim 4, containing at least one direct-dyeing dye ingredient selected from the group consisting of triphenylmethane dye compounds, aromatic nitro dye compounds, azo dye compounds and dispersion dye compounds.

8. The composition as defined in claim 4, having a pH of from 6.8 to 11.5.

9. The composition as defined in claim 4, wherein said at least one developer substance includes at least one member selected from the group consisting 1,4-diaminobenzene, 2,5-diaminotoluene, 2,5-diaminophenyl ethanol, 4-aminophenol, substituted 4-aminophenol compounds, substituted 4,5-diaminopyrazole compounds and tetraminopyrimidene and substituted tetraminopyrimidene compounds.

10. The composition as defined in claim 4, in the form of an aqueous or aqueous-alcoholic solution, a cream, a gel or an emulsion.

11. The composition as defined in claim 4, comprising a hair dye composition.

12. The composition as defined in claim 11, wherein the hair dye composition contains water and at least one cosmetic ingredient selected from the group consisting of lower aliphatic alcohols, glycerol, glycols, anionic surfactant compounds, cationic surfactant compounds, amphoteric surfactant compounds, nonionic surfactant compounds, thickeners and hair care materials.

13. The composition as defined in claim 11, wherein said p-diaminobenzene derivative compound of formula I consists of at least one member selected from the group consisting of 2,5-diamino-1-(2-pyridyl)benzene; 2,5-diamino-1-(3-pyridyl)benzene; 2,5-diamino-1-(4-pyridyl)benzene; 2,5-diamino-1-(2-pyrimidyl)benzene; 2,5-diamino-1-(6-methyl-2-pyridyl)benzene; 2,5-diamino-1-(4-methyl-2-pyridyl)-benzene; 2,5-diamino-1-(5-methyl-2-pyridyl)benzene and 2,5-diamino-1-(3-methyl-2-pyridyl)benzene.

14. The composition as defined in claim 11, wherein said at least one coupler substance is selected from the group consisting of 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di(2-hydroxyethoxy)-benzene, 1-(2-aminoethoxy)-2,4-diaminobenzene, 2-amino-1-(2-hydroxyethoxy)-4-methylaminobenzene, 2,4-diaminophenoxyacetic acid, 3-[(di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis-(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methyphenol, 5-amino-4-ethoxy-2-methylphenol, 3-amino-2,4-dicholorophenol, 5-amino-2,4-dichlorophenol, 3-amino-2-methylphenol, 3-amino-2-chloro-6-methylphenol, 3-aminophenol, 2-{(3-hydroxyphenyl)amino]acetamide, 5-[(2-hydroxyethyl)amino]-2-methylphenol, 3-[(2-hydroxyethyl)aminophenol, 3-[(2-methoxyethyl)amino]phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methy-phenol, 1-naphthol, 1,5-dihydroxynaphthalene, 1,7-dihydroxynaphthalene, 2,3-dihydoxynaphthalene, 2,7-dihydoxynaphthalene, 2-methyl-1-naphthaol acetate, 1,3-dihydoxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxy-phenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolindione.

* * * * *